US00PP22998P2

(12) United States Plant Patent
Sakhanonkho

(10) Patent No.: US PP22,998 P2
(45) Date of Patent: Aug. 28, 2012

(54) ***HEDYCHIUM* PLANT NAMED 'RAMATA'**

(50) Latin Name: *Hedychium muluense*
Varietal Denomination: Ramata

(75) Inventor: Hamidou Sakhanonkho, Hattiesburg, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/932,111

(22) Filed: Feb. 17, 2011

(51) Int. Cl.
*A01H 5/00* (2006.01)

(52) U.S. Cl. ..... Plt./373

(58) Field of Classification Search ..... Plt./373
See application file for complete search history.

*Primary Examiner* — June Hwu
*Assistant Examiner* — Louanne Krawczewicz Myers
(74) *Attorney, Agent, or Firm* — John D. Fado; Evelyn M. Rabin; Gail E. Poulos

(57) ABSTRACT

A new and distinct cultivar of *Hedychium* plant named 'Ramata', characterized by a compact, broad rounded appearance, unique leaf variegation which is uniformly distributed and stable, and mildly fragrant staminate flowers. 'Ramata' is the only *Hedychium* cultivar that combines both dwarfism and leaf variegation.

2 Drawing Sheets

Botanical designation: *Hedychium muluense.*
Cultivar denomination: 'Ramata'.

BACKGROUND OF THE INVENTION

The present invention relates to a new distinct cultivar of *Hedychium* (ornamental ginger or ginger lily) botanically known as *Hedychium muluense*, and hereinafter referred to by the name 'Ramata'.

*Hedychium* plants are suitable for landscape use, but their height (up to 2 m or more) generally limits their use as potted plants. Furthermore, *Hedychium* plants are well known for the diversity of their flower colors, but their green foliage is mostly uniform and lacks variation. To the best of our knowledge, only three variegated cultivars, 'Dr. Moy' (unpatented), 'Tahitian Flame' (U.S. Plant Pat. No. 19,921 P2), and 'Vanilla Ice' (unpatented) are commercially available as of November 2010, and these three cultivars are related. 'Tahitian Flame' occurred as a natural branch mutation of 'Dr. Moy', and 'Vanilla Ice' is a sport of 'Dr. Moy'. None of these variegated cultivars is dwarf.

Open pollinated seed were collected from greenhouse grown *Hedychium muluense* plants and regenerated in vitro in Poplarville, Miss. Callus and callus-derived somatic embryos were obtained from the in vitro regenerated plantlets. In 2007, a variegated somaclone plantlet was selected among the regenerated populations derived from somatic embryos of *Hedychium muluense*. The selected plantlet was micropropagated and plants subsequently transferred to the greenhouse in Poplarville, Miss. where they were further multiplied asexually via rhizome division and evaluated for four generations. 'Ramata' is the only *Hedychium* cultivar that combines both dwarfism and leaf variegation. The leaf variegation of Ramata is uniformly distributed and stable.

SUMMARY OF THE INVENTION

The cultivar 'Ramata' has not been observed under all possible environmental conditions. The phenotype may vary somewhat with changes in environment and cultural practices such as temperature and/or light intensity without, however, any variance in genotype.

The following traits have been repeatedly observed and are determined to be the unique characteristics of 'Ramata'. These characteristics in combination distinguish 'Ramata' as a new and distinct cultivar of *Hedychium muluense:*

1) Potted 'Ramata' plants produce multiple pseudostems originating from the rhizomes, leading to a compact, broad rounded appearance.
2) Leaf variegation in the new cultivar is more uniformly distributed than in *Hedychium* cv. 'Dr. Moy' or its two variants 'Tahitian Flame' and 'Vanilla Ice'. Furthermore, this variegation is very stable. Among the hundreds of plants produced through divisions during the last four years, not one plant reverted back to a non-variegated state.
3) 'Ramata' is the only *Hedychium* cultivar that combines both dwarfism and leaf variegation.
4) Flowers of 'Ramata' are mildly fragrant.
5) 'Ramata' has staminate flowers compared to its parent which has perfect flowers.

BRIEF DESCRIPTION OF THE PHOTOGRAPHS

The accompanying colored photographs illustrate the overall appearance of *Hedychium* 'Ramata', showing the colors as true as it is reasonably possible to obtain in colored reproductions of this type. Colors in the photographs may differ slightly from the color values cited in the detailed botanical description which accurately describes the colors of the new *Hedychium.*

DETAILED DESCRIPTION OF 'RAMATA'

Figure 1:
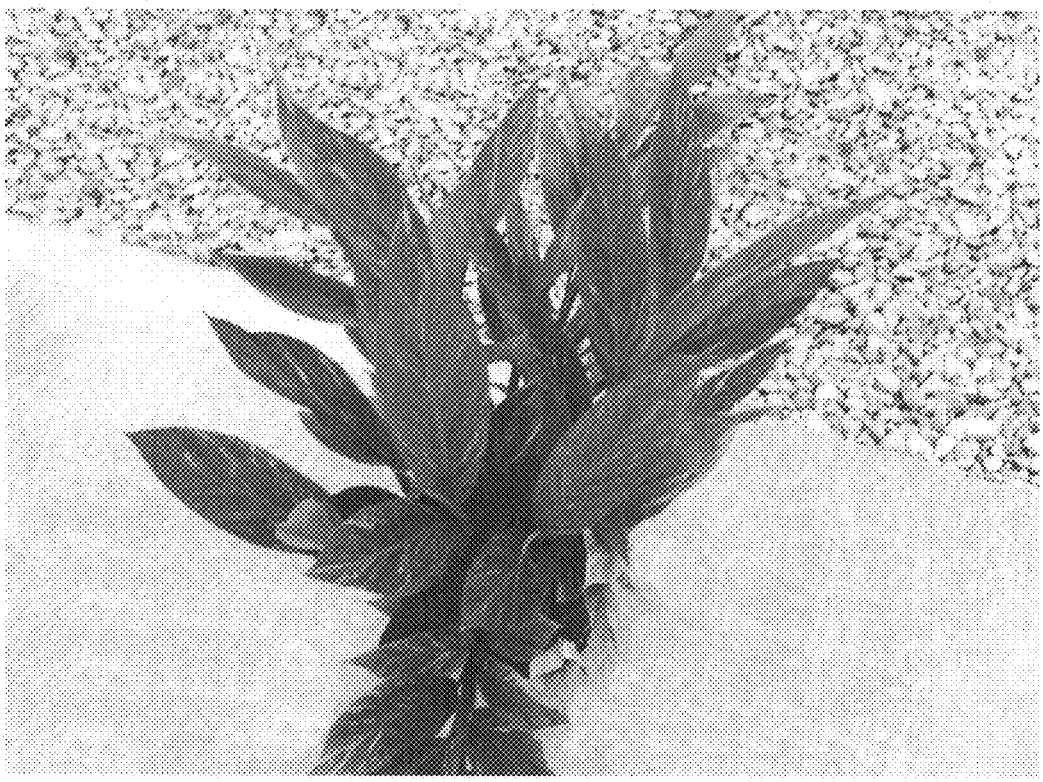
FIG. 1 is a full color photograph of a one year old *Hedychium* 'Ramata' growing in a six liter container under greenhouse conditions and located in Poplarville, Miss.
Figure 2:
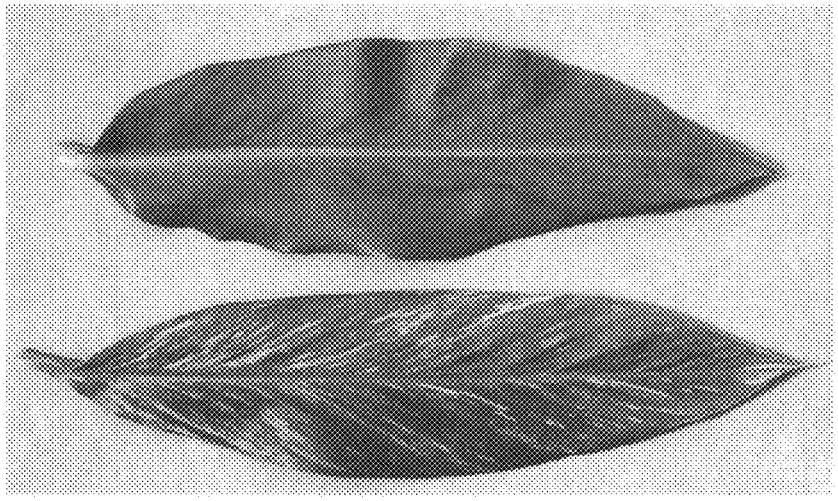
FIG. 2 is a photograph showing the leaf comparison between (bottom) *Hedychium* 'Ramata' and (top) the original non variegated *Hedychium muluense* in full color. Both images are of the adaxial (upper) side of the leaf.
Figure 3:
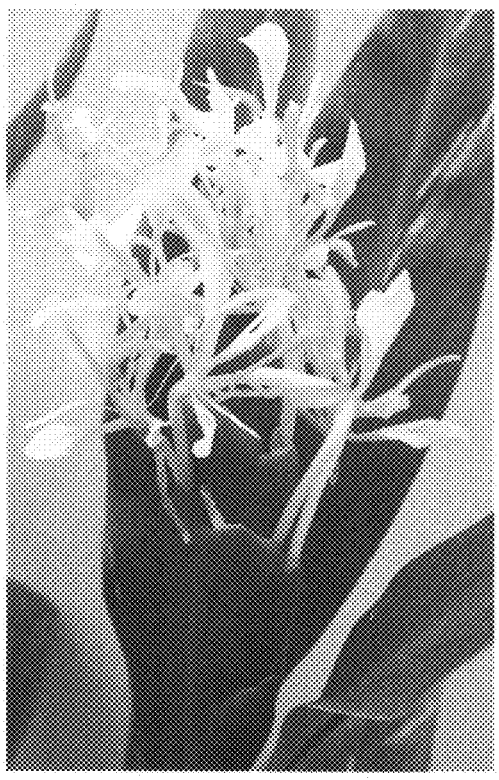
FIG. 3 is a full color photograph showing typical inflorescence at peak bloom.
Figure 4:
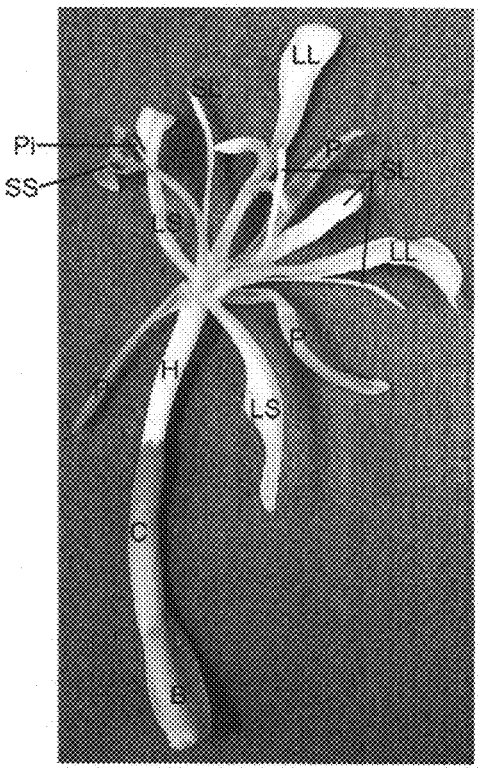
FIG. 4 is a magnified full color image of a flower with labeled components: B=bracteole, C=calyx, H=hypanthium, LL=large lobe of labellum, LS=lateral staminode, P=petal, Pi=pistil, SL=small lobe of labellum, and SS=stamen-like staminode.
Figure 5:
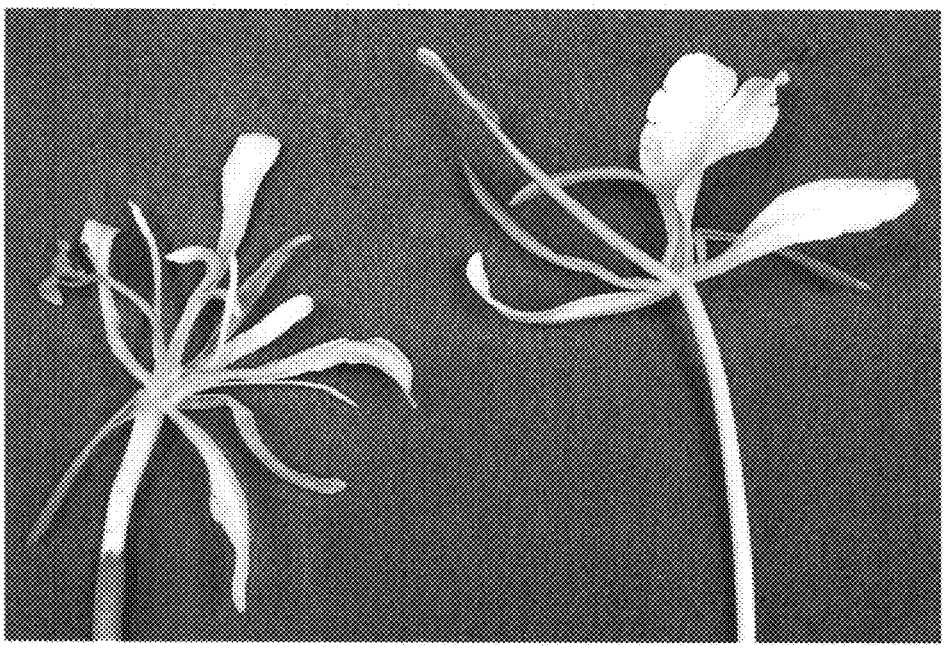
FIG. 5 is an image comparison, in full color, of floral structure, specifically the labellum, between (left) 'Ramata' and (right) the original non variegated *Hedychium muluense.*

In the following description, color references are made to The Royal Horticultural Society (R.H.S.) Colour Chart, 5th edition (2007), except where general terms of ordinary dictionary significance are used. Plants used for the photographs and description were grown for two years in a greenhouse in Poplarville, Miss.

Botanical classification: *Hedychium muluense.*

Plant description:

*Type.*—Herbaceous perennial, rhizomatous.

*Plant form and growth habit.*—Upright and clumping.

*Hardiness.*—USDA Zones 8-10.

*Plant height.*—Approximately 62.2 cm to 82.6 cm.

*Plant diameter.*—Approximately 62.0 cm to 103.0 cm.

Pseudostem:

*Form.*—Erect and reed-like.

*Length.*—Approximately 55.9 cm to 82.6 cm.

*Diameter.*—Approximately 3.1 cm to 4.9 cm.

*Internode length/leaf spacing.*—Opposite positions on pseudostem: 3.6 cm to 7.2 cm; positions on the same side of pseudostem: 6.7 cm to 14.0 cm.

*Texture.*—Glabrous.

*Color.*—Yellow-Green group 144A.

Leaf description:

*Type.*—Simple.

*Arrangement.*—Alternate, distichous (2 ranked).

*Shape.*—Oblong lanceolate.

*Length.*—Approximately 15.0 cm to 32.5 cm.

*Width.*—Approximately 6.3 cm to 10.3 cm.

*Apex.*—Attenuate.

*Base.*—Clasping sheaths with scarious stipules.

*Margin.*—Entire.

*Texture.*—Glabrous lower and upper sides, leathery.

*Venation pattern.*—Penni-parallel.

*Color.*—For adaxial surface, leaves medium green, ranging from Yellow-Green groups 144A-B to 146A-B, with varying widths of creamy white to light yellow stripes that also vary in color and include Green-Yellow 1D, Yellow-Green 145D, and Green-White 157C-D groups. For abaxial surface, leaves are a muted medium green with colors ranging from Yellow-Green groups 146-A,B, and C to Yellow-Green group 148B. The varying widths of creamy white to light yellow stripes also vary in color and include Yellow-Green group 149D and Yellow-Green group 150D.

Inflorescence:

*Type.*—Terminal dense spike with 1-3 flowers per bract.

*Length.*—Approximately 12.0 cm to 15.0 cm.

*Width.*—Approximately 3.5 cm to 8.5 cm.

*Bracts surrounding flowers.*—Lengths range from 1.8 cm to 2.5 cm; widths range from 1.8 cm to 2.3 cm; color is Yellow-Green group 144A.

*Bloom time.*—June to November under greenhouse conditions in Poplarville, Miss.

Bracteole: Encloses lower portion of the calyx; higher on one side with the opposite side having a 'v' shape. Length measurement is of the longest segment of the bracteole.

*Length.*—Approximately 1.5 cm to 2.0 cm.

*Width.*—Approximately 0.5 cm to 0.8 cm.

*Color.*—Yellow-Green group 145 A-D; gradient from light (Yellow-Green group 145D) at ovary end to dark (Yellow-Green group 145A) at upper peak.

Calyx: Encloses lower portion of the floral tube; higher on one side with the opposite side having a 'v' shape. Length measurement is of the longest segment of the calyx.

*Length.*—Approximately 3.0 cm to 3.3 cm.

*Width.*—Approximately 0.3 cm to 0.4 cm.

*Color.*—Yellow-Green group 145 A-D; gradient from light (Yellow-Green group 145D) at ovary end to dark (Yellow-Green group 145A) at upper peak.

Flower bud:

*Description.*—Slender, pointed, imbricate.

*Length.*—Approximately 1.0 cm to 2.3 cm.

*Width.*—Approximately 0.2 cm to 0.4 cm. Flower bud length was measured from the bract/bud intersection to the bud tip.

*Color.*—Gradient of color from green (Yellow-Green group 150C and 154C-D) to yellow (Yellow group 5D).

Flower:

*Type.*—Zygomorphic. Length measurement is of the longest segment of the flower (ovary to labellum tip).

*Length.*—Approximately 6.9 cm to 8.0 cm.

*Width.*—Approximately 2.7 cm to 4.6 cm.

Hypanthium (floral tube): Measurement is from the ovary to the point the petal-like structures become distinguishable.

*Length.*—Approximately 3.7 cm to 4.6 cm.

*Width.*—Approximately 0.3 cm to 0.5 cm.

Petal-like structures:

*Number.*—3 petals, 1 highly cleft labellum with multiple lobes (2 large lobes and 1-3 small lobes), and 2 lateral staminodes. Anthers have transformed to resemble petals, usually 1-4.

Petals:

*Length.*—Approximately 2.0 cm to 3.5 cm.

*Width.*—Approximately 0.2 cm to 0.4 cm.

*Color.*—Green-Yellow group 1C (upper and lower surfaces). Petals are less showy than labellum and lateral staminodes.

Labellum (highly cleft with two types of petals [usually]).

Large labellum lobes (yellow ridged):

*Length.*—2.0 cm-3.8 cm.

*Width.*—0.5 cm-0.7 cm.

*Color.*—Color descriptions are for both upper and lower surfaces. Large labellum lobes are creamy white (Yellow group 9D and 8C-D) with a medium yellow (Yellow group 13A-C) ridge extending from its base toward the lobe tip. This area has a color gradient in which the yellow is lightest toward the labellum tip and appears darker toward its base at the floral tube.

Small labellum lobes:

*Number.*—1 to 3.

*Length.*—Approximately 1.6 cm to 2.4 cm.

*Width.*—Approximately 0.1 cm to 0.3 cm.

*Color.*—Yellow group 8D (upper and lower surfaces).

Lateral staminodes:

*Number.*—2.

*Length*.—Approximately 1.8 cm to 2.5 cm.

*Width*.—Approximately 0.4 cm to 0.7 cm.

*Color*.—Color descriptions are for both upper and lower surfaces. Creamy white (Yellow group 9D and 8C-D) with a medium yellow (Yellow group 13A-C) area at the base and middle of the petal-like structure. This area has a color gradient in which the yellow is lightest toward the staminode tip and appears darker toward its base at the floral tube.

Pistil: Length measurement includes stigma, style, and ovary.

*Length*.—Approximately 4.4 cm to 6.6 cm.

*Style width*.—Consistently 0.1 cm.

*Stigma width*.—Consistently 0.2 cm.

*Color*.—Yellow group 10A-B (style) and Yellow-Green group 144A (stigma).

Stamen-like staminode (Anther/petal-like segment and filament):

*Number*.—1.

*Color*.—Yellow group 13A. Length measurement is the total length from the area of filament fusion with the floral tube to the tip of the transformed anther/petal-like segment. The width measurement is the width of the petal-like anther segment at its widest point.

*Length*.—Approximately 1.5 cm to 4.8 cm.

*Width*.—Approximately 0.4 cm to 1.8 cm.

Anther/petal-like segment:

*Color*.—Yellow group 13A. Anther/petal-like segment may have a darker coloration in place of true anther lobes and this coloration ranges among Greyed-Orange groups N167A, 167A, and 165C.

*Length*.—Approximately 1.0 cm to 3.0 cm.

*Width*.—Approximately 0.4 cm to 1.8 cm.

Filament: Section measurement excludes the transformed anther/petal-like segment.

*Color*.—Yellow group 13A.

*Length*.—Approximately 0.5 cm to 1.8 cm.

*Width*.—Consistently 0.1 cm.

Pollen: None.

Fragrance: Mildly Fragrant.

Fruit and seed: None.

Diseases and pests: Aphids, root rot, and leaf spots may occur. This plant has no known resistance.

We claim:

1. A new and distinct cultivar of *Hedychium muluense* plant named 'Ramata' substantially as illustrated and described.

* * * * *